United States Patent
Ida et al.

(10) Patent No.: US 9,394,221 B2
(45) Date of Patent: Jul. 19, 2016

(54) METHOD FOR MANUFACTURING BENZENETETRACARBOXYLIC ACID

(75) Inventors: Ryoji Ida, Tokyo (JP); Shinichiro Yanagawa, Tokyo (JP)

(73) Assignee: JX NIPPON OIL & ENERGY COMPANY, Tokyo (JP)

( * ) Notice: Subject to any disclaimer, the term of this patent is extended or adjusted under 35 U.S.C. 154(b) by 201 days.

(21) Appl. No.: 14/007,697

(22) PCT Filed: Mar. 21, 2012

(86) PCT No.: PCT/JP2012/057220
§ 371 (c)(1),
(2), (4) Date: Sep. 26, 2013

(87) PCT Pub. No.: WO2012/133061
PCT Pub. Date: Oct. 4, 2012

(65) Prior Publication Data
US 2014/0018569 A1 Jan. 16, 2014

(30) Foreign Application Priority Data

Mar. 31, 2011 (JP) ................................. 2011-080904

(51) Int. Cl.
| | | |
|---|---|---|
| C07C 51/31 | (2006.01) | |
| C10G 29/20 | (2006.01) | |
| C10G 45/44 | (2006.01) | |
| C10G 45/60 | (2006.01) | |
| C10G 55/06 | (2006.01) | |
| B01J 23/85 | (2006.01) | |
| B01J 23/882 | (2006.01) | |
| B01J 23/883 | (2006.01) | |
| B01J 23/888 | (2006.01) | |

(52) U.S. Cl.
CPC ............... *C07C 51/31* (2013.01); *C07C 51/313* (2013.01); *C10G 29/205* (2013.01); *C10G 45/44* (2013.01); *C10G 45/60* (2013.01); *C10G 55/06* (2013.01); *B01J 23/85* (2013.01); *B01J 23/882* (2013.01); *B01J 23/883* (2013.01); *B01J 23/888* (2013.01); *C10G 2300/1096* (2013.01); *C10G 2400/30* (2013.01)

(58) Field of Classification Search
None
See application file for complete search history.

(56) References Cited

U.S. PATENT DOCUMENTS

| | | | |
|---|---|---|---|
| 3,350,443 A | 10/1967 | Schlegel et al. | |
| 3,389,188 A | 6/1968 | Michalowicz | |
| 4,384,152 A | 5/1983 | Handrick et al. | |
| 5,523,505 A * | 6/1996 | Song ............................. | 585/481 |
| 2010/0056824 A1 | 3/2010 | Kitamura | |

FOREIGN PATENT DOCUMENTS

| | | |
|---|---|---|
| JP | 56-92224 | 7/1981 |
| JP | 2008-266182 | 11/2008 |

OTHER PUBLICATIONS

International Search Report issued Jun. 19, 2012 in International (PCT) Application No. PCT/JP2012/057220.
Miki et al., "Hydrocracking of Polycyclic Aromatic Compounds (4)", Journal of the Japan Institute of Energy, vol. 81, No. 11, 2002, pp. 999-1005, with English translation and cited in ISR.
Ueda et al., "Catalytic Hydrocracking of Phenanthrene over NiMo/Al$_2$O$_3$, CoMo/Al$_2$O$_3$ Catalysts and Metal-loaded Y-Zeolites", Journal of Japan Petroleum Institute, vol. 33, No. 6, 1990, pp. 413-417.
Nes et al., "The Anthrasteroid Rearrangement. II. The Structural Proof of 1-Methyl-2,3,5,6-tetracarboxybenzene", Journal of the American Chemical Society, vol. 76, 1954, pp. 3186-3188.

* cited by examiner

*Primary Examiner* — Clinton Brooks
*Assistant Examiner* — Jennifer C Sawyer
(74) *Attorney, Agent, or Firm* — Wenderoth, Lind & Ponack, L.L.P.

(57) ABSTRACT

By selectively hydrogenating a feedstock containing two or more hydrocarbons selected from the group consisting of tricyclic aromatic hydrocarbons having an anthracene skeleton and tricyclic aromatic hydrocarbons having a phenanthrene skeleton to 1,2,3,4,5,6,7,8-octahydro bodies using, as a hydrogenation catalyst, a catalyst containing two or more active metals selected from the group consisting of nickel, molybdenum, cobalt, and tungsten and then, by oxidizing the 1,2,3,4,5,6,7,8-octahydro body using a metal oxide, a benzenetetracarboxylic acid can be efficiently manufactured.

11 Claims, No Drawings

METHOD FOR MANUFACTURING BENZENETETRACARBOXYLIC ACID

FIELD

The present invention relates to a method for manufacturing 1,2,3,4-benzenetetracarboxylic acid and/or 1,2,4,5-benzenetetracarboxylic acid by: using a feedstock containing a tricyclic aromatic hydrocarbon such as anthracene and phenanthrene; selectively hydrogenating the tricyclic aromatic hydrocarbon in the feedstock; and then oxidizing the hydrogenated tricyclic aromatic hydrocarbon.

BACKGROUND

In recent years, in the field of electronic parts, as a resin excellent in heat resistance, electric characteristics, and humidity resistance, a polyimide resin has been used. As one type of feedstock for the polyimide resin, there has been used an aromatic polycarboxylic acid such as 1,2,3,4-benzenetetracarboxylic acid and 1,2,4,5-benzenetetracarboxylic acid.

Conventionally, as a method for manufacturing 1,2,3,4-benzenetetracarboxylic acid or 1,2,4,5-benzenetetracarboxylic acid, there has been known a method for oxidizing 1,2,3,4-tetramethylbenzene or 1,2,4,5-tetramethylbenzene in a liquid phase or a gas phase. As another method, there is known a method for manufacturing 1,2,4,5-benzenetetracarboxylic acid by oxidizing 2,4,5-trimethylbenzaldehyde in a liquid phase.

In addition, there has been disclosed a method for manufacturing 1,2,3,4-benzenetetracarboxylic acid or 1,2,4,5-benzenetetracarboxylic acid by: hydrogenating anthracene or phenanthrene with a metal oxide catalyst or a metal sulfide catalyst to an octahydro body thereof; and oxidizing the octahydro body with concentrated nitric acid in a liquid phase or a gas phase (see Patent Literature 1).

Furthermore, there has been disclosed a method for manufacturing 1,2,3,4-benzenetetracarboxylic acid by oxidizing 1,2,3,4,5,6,7,8-octahydrophenanthrene with potassium permanganate (see Patent Literature 2).

CITATION LIST

Patent Literature

Patent Literature 1: U.S. Pat. No. 3,350,443
Patent Literature 2: Japanese Laid-open Patent Publication No. 2008-266182

SUMMARY

Technical Problem

Now, in a petroleum refining process, a vacuum gas oil is cracked by a fluid catalytic cracking (FCC) units to manufacture mainly a gasoline base material, petrochemical products, and the like. Heavy oil generated simultaneously in this process is known to contain a large amount of polycyclic aromatic hydrocarbons. For example, light cycle oil (LCO), which is a cracked gas oil, has a relatively large content of a bicyclic aromatic hydrocarbon and has been utilized as a light oil or a heavy oil.

However, in recent years, it has been studied to manufacture benzene, toluene, xylene, and the like, which have a higher added value from LCO. In a similar way, there has been searched a method for converting also a fraction heavier than LCO, that is, a fraction containing a relatively large amount of a tricyclic aromatic hydrocarbon to a compound having a higher added value.

The present invention has been achieved by taking into consideration the viewpoint of effectively utilizing a residual oil (called also bottom oil) of a FCC units containing a tricyclic aromatic hydrocarbon, and it is an object of the present invention to provide a method for efficiently manufacturing a benzenetetracarboxylic acid from a feedstock containing two or more hydrocarbons selected from tricyclic aromatic hydrocarbons having an anthracene skeleton and tricyclic aromatic hydrocarbons having a phenanthrene skeleton.

Solution to Problem

To solve the problem described above, a method for manufacturing a benzenetetracarboxylic acid according to the present invention comprises: a hydrogenation reaction step for generating, by hydrogenating a feedstock containing two or more hydrocarbons selected the group consisting of tricyclic aromatic hydrocarbons having an anthracene skeleton represented by General Formula (I):

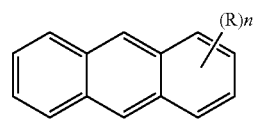

(where R is a linear or branched alkyl group and n represents the number of substituents on the anthracene skeleton and is an integer of 0 to 8, with the proviso that R is located at 1-position to 8-position and when n is 2 to 8, Rs are optionally alkyl groups having the same number of or different numbers of carbon atoms)
and tricyclic aromatic hydrocarbons having a phenanthrene skeleton represented by General Formula (II):

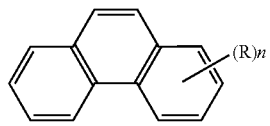

(where R is a linear or branched alkyl group and n represents the number of substituents on the phenanthrene skeleton and is an integer of 0 to 8, with the proviso that R is located at 1-position to 8-position and when n is 2 to 8, Rs are optionally alkyl groups having the same number of or different numbers of carbon atoms), two or more hydrocarbons selected from the group consisting of hydrocarbons having a 1,2,3,4,5,6,7,8-octahydroanthracene skeleton represented by General Formula (III):

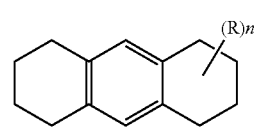

(where R is a linear or branched alkyl group and n represents the number of substituents on the 1,2,3,4,5,6,7,8-octahydroanthracene skeleton and is an integer of 0 to 8, with the proviso that R is located at 1-position to 8-position and when n is 2 to 8, Rs are optionally alkyl groups having the same number of or different numbers of carbon atoms) and hydrocarbons having a 1,2,3,4,5,6,7,8-octahydrophenanthrene skeleton represented by General Formula (IV):

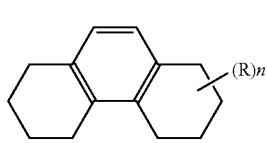

(IV)

(where R is a linear or branched alkyl group and n represents the number of substituents on the 1,2,3,4,5,6,7,8-octahydrophenanthrene skeleton and is an integer of 0 to 8, with the proviso that R is located at 1-position to 8-position and when n is 2 to 8, Rs are optionally alkyl groups having the same number of or different numbers of carbon atoms)
using, as a hydrogenation catalyst, a catalyst containing two or more active metals selected from the group consisting of nickel, molybdenum, cobalt, and tungsten; and an oxidation reaction step for oxidizing, with a metal oxide, two or more hydrocarbons selected from the group consisting of hydrocarbons having a 1,2,3,4,5,6,7,8-octahydroanthracene skeleton represented by General Formula (III) and hydrocarbons having a 1,2,3,4,5,6,7,8-octahydrophenanthrene skeleton represented by General Formula (IV) that are generated at the hydrogenation reaction step.

Moreover, in the method for manufacturing a benzenetetracarboxylic acid according to the above-deescribed invention, in General Formulae (I), (II), (III), and (IV), R is a $C_{1-4}$ linear or branched alkyl group.

Moreover, in the method for manufacturing a benzenetetracarboxylic acid according to the above-deescribed invention, in General Formulae (I), (II), (III), and (IV), R is a linear or branched alkyl group and n represents the number of substituents on the anthracene skeleton, the phenanthrene skeleton, the 1,2,3,4,5,6,7,8-octahydroanthracene skeleton, and the 1,2,3,4,5,6,7,8-octahydrophenanthrene skeleton and is an integer of 0 to 4.

Moreover, in the method for manufacturing a benzenetetracarboxylic acid according to the above-deescribed invention, the feedstock contains a fraction at 340 to 420° C.

Moreover, in the method for manufacturing a benzenetetracarboxylic acid according to the above-deescribed invention, the feedstock is derived from petroleum or derived from coal.

Moreover, in the method for manufacturing a benzenetetracarboxylic acid according to the above-deescribed invention, the metal oxide is potassium permanganate or potassium dichromate.

Moreover, in the method for manufacturing a benzenetetracarboxylic acid according to the above-deescribed invention, the hydrogenation reaction step is a step for selectively hydrogenating the feedstock with the hydrogenation catalyst in the presence of hydrogen at a reaction temperature of 200 to 400° C. and under a reaction pressure of 2 to 15 MPa.

Moreover, in the method for manufacturing a benzenetetracarboxylic acid according to the above-described invention, the oxidation reaction step is a step for oxidizing the hydrogenation reaction product of the feedstock with the metal oxide in the presence of an additive at a reaction temperature of 50 to 150° C. and under a reaction pressure of normal pressure to 1 MPa.

Moreover, the method for manufacturing a benzenetetracarboxylic acid according to the above-deescribed invention further comprises, before the oxidation reaction step: an isomerization reaction step for isomerizing a hydrocarbon having a 1,2,3,4,5,6,7,8-octahydrophenanthrene skeleton represented by General Formula (IV):

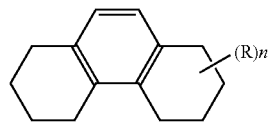

(IV)

(where R is a linear or branched alkyl group and n represents the number of substituents on the 1,2,3,4,5,6,7,8-octahydrophenanthrene skeleton and is an integer of 0 to 8, with the proviso that R is located at 1-position to 8-position and when n is 2 to 8, Rs are optionally alkyl groups having the same number of or different numbers of carbon atoms) to a hydrocarbon having a 1,2,3,4,5,6,7,8-octahydroanthracene skeleton represented by General Formula (III):

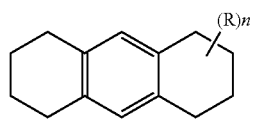

(III)

(where R is a linear or branched alkyl group and n represents the number of substituents on the 1,2,3,4,5,6,7,8-octahydroanthracene skeleton and is an integer of 0 to 8, with the proviso that R is located at 1-position to 8-position and when n is 2 to 8, Rs are optionally alkyl groups having the same number of or different numbers of carbon atoms) with an acid catalyst.

Moreover, in the method for manufacturing a benzenetetracarboxylic acid according to the above-deescribed invention, in General Formulae (IV) and (III), R is a $C_{1-4}$ linear or branched alkyl group.

Moreover, in the method for manufacturing a benzenetetracarboxylic acid according to the above-deescribed invention, in General Formulae (IV) and (III), R is a $C_{1-4}$ linear or branched alkyl group and n represents the number of substituents of the hydrocarbon having the 1,2,3,4,5,6,7,8-octahydrophenanthrene skeleton and the hydrocarbon having the 1,2,3,4,5,6,7,8-octahydroanthracene skeleton and is an integer of 0 to 4.

Advantageous Effects of Invention

The method for manufacturing a benzenetetracarboxylic acid according to the present invention can efficiently manufacture a benzenetetracarboxylic acid from a mixture of tricyclic aromatic hydrocarbons having various types of side chains by: selectively hydrogenating a feedstock such as a residual oil containing a tricyclic aromatic hydrocarbon; and then oxidizing the hydrogenated feedstock.

DESCRIPTION OF EMBODIMENTS

<Feedstock>
First, the feedstock for manufacturing the benzenetetracarboxylic acid used in the present invention is described. In the present invention, there is used a feedstock containing two or more hydrocarbons selected from the group consisting of tricyclic aromatic hydrocarbons having an anthracene skeleton represented by General Formula (I):

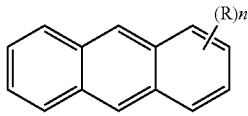

(I)

and tricyclic aromatic hydrocarbons having a phenanthrene skeleton represented by General Formula (II):

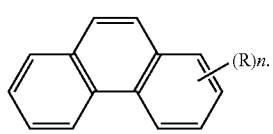

(II)

In the tricyclic aromatic hydrocarbons represented by General Formula (I) and General Formula (II), R represents a substituent on the anthracene skeleton or the phenanthrene skeleton, specifically a linear or branched alkyl group and is preferably a $C_{1-4}$ linear or branched alkyl group, and preferred examples of the alkyl group may include a methyl group, an ethyl group, a propyl group, and a butyl group. n represents the number of substituents with which the anthracene skeleton or the phenanthrene skeleton is substituted and n is an integer of 0 to 8, preferably an integer of 0 to 4, and more preferably an integer of 0 to 3. When a tricyclic aromatic hydrocarbon has two or more substituents R, Rs may be alkyl groups having the same number of carbon atoms or different numbers of carbon atoms.

When a feedstock derived from petroleum or derived from coal is used, some of these feedstocks can contain, besides the tricyclic aromatic hydrocarbon, a bicyclic aromatic hydrocarbon such as naphthalenes or a tetracyclic aromatic hydrocarbon such as pyrenes in most cases. In the present invention, the feedstock containing a monocyclic aromatic hydrocarbon or a polycyclic aromatic hydrocarbon such as a bicyclic aromatic hydrocarbon and a tetra- or more cyclic aromatic hydrocarbon causes no substantial problem; however, these aromatic hydrocarbons by-produce finally a carboxylic acid other than a benzenetetracarboxylic acid that is the objective product through the hydrogenation reaction step and the oxidation reaction step. For this reason, their contents are preferably kept small. For causing the feedstock to contain a large amount of a tricyclic aromatic hydrocarbon necessary for the present invention and for reducing the mixing of a monocyclic aromatic hydrocarbon or a bicyclic aromatic hydrocarbon into the feedstock, it is preferred to cause the feedstock to have a boiling point of 340° C. (boiling point of phenanthrene). When the feedstock has a boiling point of 340° C. or more, without reducing the content of the tricyclic aromatic hydrocarbon in the feedstock, the mixing of a monocyclic aromatic hydrocarbon or a bicyclic aromatic hydrocarbon into the feedstock can be reduced. In addition, when the feedstock has a boiling point of 420° C. or less, a tetracyclic aromatic hydrocarbon having an alkyl group can be excluded from the feedstock and when the feedstock has a boiling point of 395° C. or less, without reducing the content of the tricyclic aromatic hydrocarbon, the mixing of a tetra- or more cyclic aromatic hydrocarbon can be reduced. As examples, the boiling points of tricyclic aromatic hydrocarbons and tetracyclic aromatic hydrocarbons such as pyrenes are listed in Table 1.

TABLE 1

| Compound name | Boiling point (° C.) |
| --- | --- |
| Phenanthrene | 340 |
| Anthracene | 342 |
| 1-methylphenanthrene | 351 |
| 1-methylanthracene | 353 |
| 2-ethylphenanthrene | 368 |
| 2-ethylanthracene | 356 |
| 1,2-dimethylphenanthrene | 375 |
| 3,5-dimethylphenanthrene | 375 |
| 1,4-dimethylanthracene | 371 |
| 2,3-dimethylanthracene | 372 |
| 2-propylanthracene | 381 |
| 2-isopropylanthracene | 371 |
| 1,2,4-trimethylanthracene | 390 |
| 1,3,6-trimethylanthracene | 390 |
| 1,2,3,4-tetramethylphenanthrene | 410 |
| 1,3,6,7-tetramethylanthracene | 409 |
| 1,4,6,7-tetramethylanthracene | 408 |
| 9,10-diethyl-3,4-dimethylanthracene | 430 |
| Pyrene | 395 |
| 1-methylpyrene | 431 |

Accordingly, the feedstock derived from petroleum or derived from coal used in the present invention mainly contains preferably a fraction of 340° C. to 420° C. and more preferably a fraction of 340° C. to 395° C.

From Table 1, in the tricyclic aromatic hydrocarbons represented by General Formulae (I) and (II), although R is not particularly limited, when R is a substituent having a $C_{1-4}$ linear or branched alkyl group and preferably a substituent having a $C_{1-3}$ linear or branched alkyl group, the feedstock has a boiling point in the range preferred for the present invention. When R is a $C_5$ or more linear or branched alkyl group, the feedstock contains a large amount of hydrocarbons having a boiling point of more than 420° C., so that a large amount of tetracyclic aromatic hydrocarbons unnecessary for the present invention is mixed, which is not preferred. Examples of the substituent preferred for the present invention may include a methyl group, an ethyl group, a propyl group, an isopropyl group, and a butyl group. Although the position of the substituent R is also not particularly limited, R is preferably located at 1- to 8-position of the anthracene skeleton or the phenanthrene skeleton. When the tricyclic aromatic hydrocarbon is a tricyclic aromatic hydrocarbon having a substituent at 9-position or 10-position, the substituent at 9-position or 10-position is also oxidized in the oxidation reaction step to be converted into a carboxy group, so that it is difficult to obtain a benzenetetracarboxylic acid that is the objective product of the present invention.

In the tricyclic aromatic hydrocarbons represented by General Formulae (I) and (II), although n is not particularly limited, when n is 0 to 4, preferably 0 to 3, the feedstock has a preferred boiling point range. The larger n is, the higher the boiling point of the hydrocarbon is elevated, so that a large amount of tetracyclic aromatic hydrocarbons unnecessary for the present invention is mixed. In addition, the progression of hydrogenation of the anthracene skeleton or the phenanthrene skeleton is difficult and the hydrogenation reaction under a higher pressure is required, which is not preferred. When a tricyclic aromatic hydrocarbon has two or more substituents R, Rs may be alkyl groups having the same number of carbon atoms or different numbers of carbon atoms.

Examples of the tricyclic aromatic hydrocarbon preferred for the present invention among the tricyclic aromatic hydrocarbons having an anthracene skeleton represented by General Formula (I) may include, besides anthracene, 1-methylanthracene, 1,4-dimethylanthracene, 2,3-dimethylanthracene, 1,2,4-trimethylanthracene, 1,3,6-trimethylanthracene, 1,3,6,7-tetramethylanthracene, 1,4,6,7-tetramethylanthracene, 2-ethylanthracene, 2-n-propylanthracene, and 2-isopropylanthracene.

Examples of the tricyclic aromatic hydrocarbon preferred for the present invention among the tricyclic aromatic hydrocarbons having a phenanthrene skeleton represented by General Formula (II) may include, besides phenanthrene, 1-methylphenanthrene, 1,2-dimethylphenanthrene, 3,5-dimethylphenanthrene, 1,2,3,4-tetramethylphenanthrene, and 2-ethylphenanthrene.

Examples of the feedstock containing two or more hydrocarbons selected from the group consisting of the tricyclic aromatic hydrocarbons having an anthracene skeleton and the tricyclic aromatic hydrocarbons having a phenanthrene skeleton that are exemplified above may include stock oils derived from petroleum or derived from coal.

Examples of the stock oil derived from petroleum containing two or more hydrocarbons selected from the group consisting of the tricyclic aromatic hydrocarbons having an anthracene skeleton represented by General Formula (I) and the tricyclic aromatic hydrocarbons having a phenanthrene skeleton represented by General Formula (II) may include: an atmospheric residue; a vacuum residual oil; a coker oil; a synthetic crude oil; a heavy gas oil; a vacuum gas oil; and LCO, HCO (heavy cycle oil), and CLO (clarified oil), which are a heavy fraction obtained from the FCC apparatus. Among them, preferred are HCO, CLO, a coker oil, and the like having a high content of the tricyclic aromatic hydrocarbon.

Examples of the stock oil derived from coal containing two or more hydrocarbons selected from the group consisting of the tricyclic aromatic hydrocarbons having an anthracene skeleton represented by General Formula (I) and the tricyclic aromatic hydrocarbons having a phenanthrene skeleton represented by General Formula (II) may include a coal tar oil, an anthracene oil, an anthracene cake, and a creosote oil. Among them, preferred is an anthracene oil having a high content of the tricyclic aromatic hydrocarbon that is produced by distilling a coal tar oil and fractionating a fraction at a temperature of 330 to 380° C.

As the stock oil derived from petroleum or derived from coal containing two or more hydrocarbons selected from the tricyclic aromatic hydrocarbons having an anthracene skeleton and the tricyclic aromatic hydrocarbons having a phenanthrene skeleton, the above-exemplified oils can be used as they are as the feedstock. Furthermore, the feedstock may be further distilled to contain a fraction at 340 to 420° C., preferably a fraction at 340 to 395° C.

Next, the hydrogenation reaction step that is a first step of the method for manufacturing the benzenetetracarboxylic acid of the present invention is described.

<Hydrogenation Reaction Step>

The hydrogenation reaction step of the present invention is a step for selectively hydrogenating a feedstock containing two or more hydrocarbons selected from the group consisting of the tricyclic aromatic hydrocarbons having an anthracene skeleton represented by General Formula (I) and the tricyclic aromatic hydrocarbons having a phenanthrene skeleton represented by General Formula (II) to a hydrocarbon selected from the group consisting of hydrocarbons having a 1,2,3,4,5,6,7,8-octahydroanthracene skeleton represented by General Formula (III):

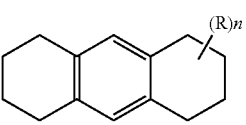

and hydrocarbons having a 1,2,3,4,5,6,7,8-octahydrophenanthrene skeleton represented by General Formula (IV):

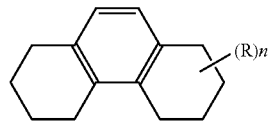

by a method including: using, as a hydrogenation catalyst, a catalyst containing two or more active metals selected from the group consisting of nickel, molybdenum, cobalt, and tungsten; subjecting the hydrogenation catalyst to sulfuration treatment; and subjecting the feedstock to the hydrogenation reaction.

In the hydrocarbons represented by General Formulae (III) and (IV), R represents a substituent on the 1,2,3,4,5,6,7,8-octahydroanthracene skeleton or the 1,2,3,4,5,6,7,8-octahydrophenanthrene skeleton and specifically a linear or branched alkyl group and n represents the number of substituents with which the 1,2,3,4,5,6,7,8-octahydroanthracene skeleton or the 1,2,3,4,5,6,7,8-octahydrophenanthrene skeleton is substituted.

Although R is not particularly limited, R is preferably a substituent having a $C_{1-4}$ linear or branched alkyl group and more preferably a substituent having a $C_{1-3}$ linear or branched alkyl group. When R is a $C_5$ or more linear or branched alkyl group, a large amount of hydrogenated products of tetracyclic aromatic hydrocarbons unnecessary for the present invention is mixed, which is not preferred. Examples of the substituent preferred for the present invention may include a methyl group, an ethyl group, a propyl group, an isopropyl group, and a butyl group. The substituent R is located at 1- to 8-position of the anthracene skeleton or the phenanthrene skeleton. When the tricyclic aromatic hydrocarbon is a tricyclic aromatic hydrocarbon having a substituent at 9-position or 10-position, the substituent at 9-position or 10-position is also oxidized in the oxidation reaction step to be converted into a carboxy group, so that it is difficult to obtain a benzenetetracarboxylic acid that is the objective product of the present invention.

In the hydrogenated product of the tricyclic aromatic hydrocarbons represented by General Formulae (III) and (IV), although n is not particularly limited, n is preferably 0 to 4 and more preferably 0 to 3. The larger n is, the higher the boiling point of the feedstock is elevated, so that a large amount of hydrogenated products of tetracyclic aromatic hydrocarbons unnecessary for the present invention is mixed, which is not preferred. When the hydrogenated product of the tricyclic aromatic hydrocarbon has two or more substituents R, Rs may be alkyl groups having the same number of carbon atoms or different numbers of carbon atoms.

Examples of the hydrocarbon preferred for the present invention among the hydrocarbons having a 1,2,3,4,5,6,7,8-octahydroanthracene skeleton represented by General Formula (III) may include, besides 1,2,3,4,5,6,7,8-octahydroanthracene, 1-methyl-1,2,3,4,5,6,7,8-octahydroanthracene, 1,4-dimethyl-1,2,3,4,5,6,7,8-octahydroanthracene, 2,3-dimethyl-1,2,3,4,5,6,7,8-octahydroanthracene, 1,2,4-trimethyl-1,2,3,4,5,6,7,8-octahydroanthracene, 1,3,6-trimethyl-1,2,3,4,5,6,7,8-octahydroanthracene, 1,3,6,7-tetramethyl-1,2,3,4,5,6,7,8-octahydroanthracene, 1,4,6,7-tetramethyl-1,2,3,4,5,6,7,8-octahydroanthracene, 2-ethyl-1,2,3,4,5,6,7,8-octahydroanthracene, 2-n-propyl-1,2,3,4,5,6,7,8-octahydroanthracene, and 2-isopropyl-1,2,3,4,5,6,7,8-octahydroanthracene.

Examples of the hydrocarbon preferred for the present invention among the hydrocarbons having a 1,2,3,4,5,6,7,8-octahydrophenanthrene skeleton represented by General Formula (IV) may include, besides 1,2,3,4,5,6,7,8-octahydrophenanthrene, 1-methyl-1,2,3,4,5,6,7,8-octahydrophenanthrene, 1,2-dimethyl-1,2,3,4,5,6,7,8-octahydrophenanthrene, 3,5-dimethyl-1,2,3,4,5,6,7,8-octahydrophenanthrene, 1,2,3,4-tetramethyl-1,2,3,4,5,6,7,8-octahydrophenanthrene, and 2-ethyl-1,2,3,4,5,6,7,8-octahydrophenanthrene.

An object of the present step is to efficiently hydrogenate aromatic rings at both terminals of the tricyclic aromatic hydrocarbon other than an aromatic ring at the center of the tricyclic aromatic hydrocarbon to obtain a benzenetetracarboxylic acid efficiently in a later oxidation step. For the present step, it is important that while the hydrogenation is progressed so as to reduce the amount of a bicyclic aromatic hydrocarbon in which only one aromatic ring is hydrogenated, the generation of a saturated hydrocarbon such as perhydroanthracene by complete hydrogenation of the tricyclic aromatic hydrocarbon and an excessive hydrocracking reaction are suppressed.

For achieving such hydrogenation, in the hydrogenation reaction step of the present invention, as described above, a catalyst having two or more active metals selected from the group consisting of nickel, molybdenum, cobalt, and tungsten is used as a hydrogenation catalyst; the hydrogenation catalyst is subjected to sulfuration treatment; and then, the feedstock containing two or more hydrocarbons selected from the group consisting of the tricyclic aromatic hydrocarbons having an anthracene skeleton represented by General Formula (I) and the tricyclic aromatic hydrocarbons having a phenanthrene skeleton represented by General Formula (II), is hydrogenated.

The stock oil derived from petroleum or derived from coal and containing the tricyclic aromatic hydrocarbon generally contains a large amount of sulfur content that is difficult to be completely removed. Accordingly, when the hydrogenation is performed, for example, using a noble metal catalyst, the hydrogenation catalyst suffers poisoning by the sulfur content, so that the noble metal catalyst is not suitable to be used. On the other hand, when the hydrogenation catalyst is a catalyst exhibiting hydrogenation activity in a state of a metal sulfide thereof, the catalyst does not suffer poisoning by the sulfur content and can maintain the activity, so that, in the present invention, it is preferred to use a catalyst having an active metal exhibiting hydrogenation activity in a state of a metal sulfide thereof. However, the noble metal catalyst can be used in the case where the sulfur content is removed from stock oil subjected to the hydrogenation reaction step to reduce the content down to the level that can allow the use of the noble metal catalyst.

Examples of the catalyst exhibiting hydrogenation activity in a state of a metal sulfide thereof may include the nickel catalyst, the cobalt catalyst, a nickel-molybdenum catalyst, a cobalt-molybdenum catalyst, and a nickel-tungsten catalyst. As a combination of two active metals in a hydrogenation catalyst, from high reaction activity of hydrogenation, cobalt and molybdenum, and nickel and molybdenum are preferred and nickel and molybdenum is more preferred. These catalysts have high reaction activity of the hydrogenation reaction, so that it is possible to maximize the yield of the hydrocarbon having an octahydroanthracene skeleton and/or the hydrocarbon having an octahydrophenanthrene skeleton and furthermore, to suppress excessive hydrogenation and excessive hydrocracking reaction while reducing the hydrogenation reaction pressure to a low pressure.

The catalyst having selected two or more active metals is preferably used as a catalyst supported on a carrier. By supporting an active metal on a carrier, the surface area of the active metal can be enhanced and reaction activity of the hydrogenation reaction can be enhanced. Although the carrier is not particularly limited, as the carrier, for example, alumina, silica, titania, and the like can be used.

The reaction temperature for the hydrogenation reaction step of the present invention is preferably a range of 200 to 400° C. and more preferably a range of 250 to 380° C. When the reaction temperature is higher than 200° C., the hydrogenation conversion of the tricyclic aromatic hydrocarbon can be satisfactorily enhanced and when the reaction temperature is lower than 400° C., excessive hydrogenation and an excessive hydrocracking reaction can be suppressed, so that the yield of the hydrocarbon having an octahydroanthracene skeleton and/or the hydrocarbon having an octahydrophenanthrene skeleton can be maximized.

The reaction pressure for the hydrogenation reaction step of the present invention is preferably a range of 2 to 15 MPa and more preferably a range of 3 to 10 MPa. When the reaction pressure is higher than 2 MPa, the hydrogenation conversion of the tricyclic aromatic hydrocarbon is satisfactory and on the other hand, when the reaction pressure is lower than 15 MPa, excessive hydrogenation and an excessive hydrocracking reaction can be suppressed, so that the yield of the hydrocarbon having an octahydroanthracene skeleton and/or the hydrocarbon having an octahydrophenanthrene skeleton can be maximized. By lowering the reaction pressure than 15 MPa, a hydrogenation apparatus having a relatively low tolerable pressure can be used, so that the cost of equipment can be reduced.

The reaction format of the hydrogenation reaction step of the present invention is not particularly limited. That is, a batch type reaction vessel such as an autoclave can be used and a flow type reaction vessel can also be used.

When the hydrogenation reaction step is performed using a batch type reaction vessel, the reaction time of the hydrogenation reaction is preferably a range of 1 to 20 hour(s) and more preferably a range of 2 to 10 hours. When the reaction time is longer than 1 hour, the hydrogenation conversion of the tricyclic aromatic hydrocarbon can be satisfactorily enhanced and on the other hand, when the reaction time is shorter than 20 hours, excessive hydrogenation and an excessive hydrocracking reaction can be suppressed, so that the yield of the hydrocarbon having an octahydroanthracene skeleton and/or the hydrocarbon having an octahydrophenanthrene skeleton can be maximized. Furthermore, by shortening the reaction time than 20 hours, the productivity can be enhanced.

On the other hand, when the hydrogenation reaction step is performed using a flow type reaction vessel, the liquid hourly space velocity (LHSV) is preferably $0.1\ h^{-1}$ or more and $20\ h^{-1}$ or less, more preferably $0.2\ h^{-1}$ or more and $10\ h^{-1}$ or less. When LHSV is set at $20\ h^{-1}$ or less, the tricyclic aromatic hydrocarbon can be satisfactorily hydrogenated under a lower hydrogenation reaction pressure. On the other hand, by setting LHSV at $0.1\ h^{-1}$ or more, excessive hydrogenation and an excessive hydrocracking reaction can be suppressed, so that the yield of the hydrocarbon having an octahydroanthracene skeleton and/or the hydrocarbon having an octahydrophenanthrene skeleton can be maximized. Furthermore, by setting LHSV at 0.1 h$^{-1}$ or more, the increasing in size of the hydrogenation reaction vessel can be avoided.

<Oxidation Reaction Step>

Subsequently, the oxidation reaction step that is a second step of the method for manufacturing the benzenetetracarboxylic acid of the present invention is described.

The oxidation reaction step of the present invention is a step of oxidizing, with a metal oxide, two or more hydrocarbons selected from the group consisting of hydrocarbons having a 1,2,3,4,5,6,7,8-octahydroanthracene skeleton represented by General Formula (III) and hydrocarbons having a 1,2,3,4,5,6,7,8-octahydrophenanthrene skeleton represented by General Formula (IV) that are produced by being hydrogenated in the hydrogenation reaction step to obtain 1,2,4,5-benzenetetracarboxylic acid represented by General Formula (V):

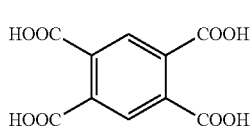

(V)

and/or 1,2,3,4-benzenetetracarboxylic acid represented by General Formula (VI):

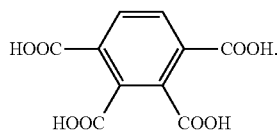

(VI)

In the case where a feedstock derived from petroleum or derived from coal is used, even when the hydrocarbon contained in the v is limited to a hydrocarbon having a tricyclic aromatic hydrocarbon skeleton, generally, in the hydrocarbons contained in the feedstock, the positions and the numbers of the alkyl group are different from each other, so that the hydrocarbon can be many types of hydrocarbons. However, according to the present invention, by hydrogenating the hydrocarbon in the feedstock and by oxidizing the hydrogenated hydrocarbon with a strong oxidant, most of cyclohexyl rings with alkyl groups bonded to the aromatic ring can be converted into a carboxylic acid and as the result thereof, the number of components contained in the product can be largely reduced.

More specifically, according to the manufacturing method of the present invention, even when as the starting feedstock, there is used stock oil derived from petroleum or derived from coal and containing a plurality of types of tricyclic aromatic hydrocarbons, for example, anthracenes and/or phenanthrenes having one or more alkyl group(s) at different positions other than 9-position and 10-position or anthracenes and/or phenanthrenes having alkyl groups having different carbon numbers at the same position other than 9-position and 10-position, by hydrogenating the stock oil and by oxidizing the resultant hydrogenated product in the above-described oxidation reaction step, the cyclohexyl ring is cut, so that irrespective of the presence or absence and the type of a substituent at a position other than 9-position and 10-position, 1,2,4,5-benzenetetracarboxylic acid and/or 1,2,3,4-benzenetetracarboxylic acid can be obtained. In addition, when the feedstock contains a tricyclic aromatic hydrocarbon having a substituent at 9-position or 10-position, although there is the possibility that from such a hydrocarbon, benzenepentacarboxylic acid or benzenehexacarboxylic acid is generated, even in such a case, by performing the purification in the separation step in the latter part, 1,2,4,5-benzenetetracarboxylic acid and/or 1,2,3,4-benzenetetracarboxylic acid can be obtained as a main component.

For example, as expressed by Chemical Reaction Formula (VII) below, 1,2,5,6-tetramethylanthracene (compound A) can be exemplified as an example of the tricyclic aromatic hydrocarbon having an anthracene skeleton represented by General Formula (I). 1,2,5,6-tetramethylanthracene (compound A) is hydrogenated in the hydrogenation reaction step to 1,2,5,6-tetramethyl-1,2,3,4,5,6,7,8-octahydroanthracene (compound B) that is further oxidized in the oxidation reaction step to 1,2,4,5-benzenetetracarboxylic acid (compound C).

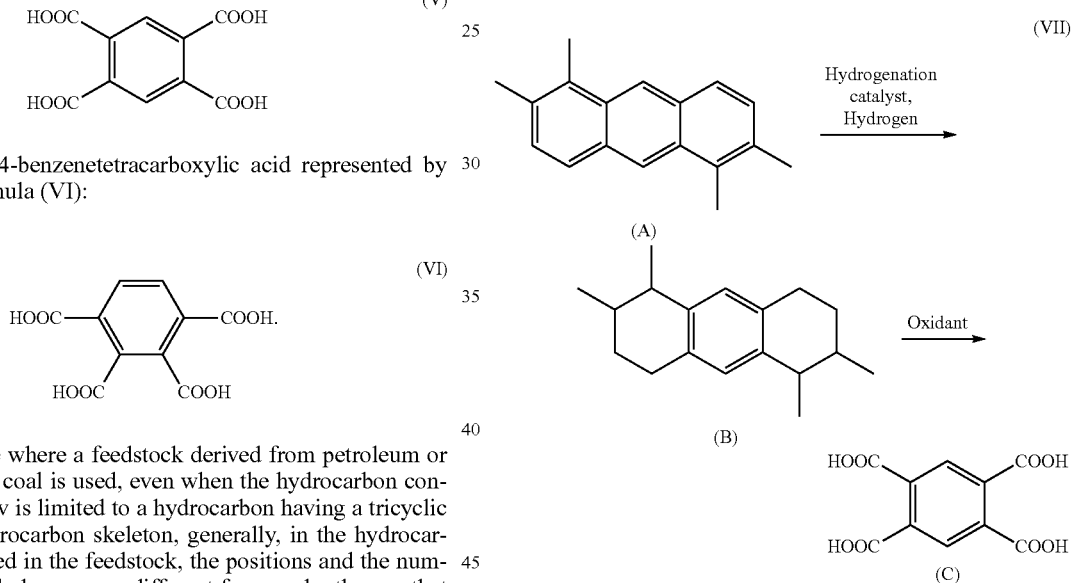

(VII)

In the oxidation reaction step of the present invention, a carbon-carbon bond forming a cyclohexyl ring of an octahydro body is oxidatively cut, so that as in Chemical Reaction Formula (VII), also from a tricyclic aromatic hydrocarbon having a plurality of alkyl side chains such as 1,2,5,6-tetramethylanthracene (compound A), by the same step as in the case of an anthracene having no side chain without performing any other step, 1,2,4,5-benzenetetracarboxylic acid having no alkyl side chain can be obtained. Accordingly, in the feedstock of the present invention, even when there are mixed two or more hydrocarbon feedstocks selected from the group consisting of tricyclic aromatic hydrocarbons having an anthracene skeleton represented by General Formula (I) having different alkyl side chains and tricyclic aromatic hydrocarbons having a phenanthrene skeleton represented by General Formula (II) having different alkyl side chains, by the same reaction step as in the case of an anthracene or a phenanthrene having no side chain, 1,2,4,5-benzenetetracarboxylic acid and/or 1,2,3,4-benzenetetracarboxylic acid with a high purity can be obtained.

In the oxidation reaction step, although depending on the degree of the progression of the oxidation reaction, benzenecarboxylic acids in some forms (for example, dicarboxylic acid, tricarboxylic acid, and the like) are generated, it is satisfactory that tetracarboxylic acid can be obtained as the main component. By performing purification in a separation step after the oxidation reaction step, a benzenetetracarboxylic acid can be obtained.

The oxidant used in the oxidation reaction step of the present invention is preferably a strong metal oxide capable of achieving the above-described oxidation. Preferred examples of the oxidant used for liquid phase oxidation may include a metal oxide such as potassium permanganate and potassium dichromate. When potassium permanganate or potassium dichromate is used, for example, by liquid phase oxidation using water as a solvent, two or more hydrocarbons selected from the group consisting of hydrocarbons having a 1,2,3,4,5,6,7,8-octahydroanthracene skeleton and hydrocarbons having a 1,2,3,4,5,6,7,8-octahydrophenanthrene skeleton are oxidized.

When liquid phase oxidation is performed using water as a solvent, oxidation is performed using, as an additive, a surfactant such as sodium dodecylbenzenesulfonate and manganese (II) dodecylbenzenesulfonate. By adding the additive to the reaction system, the oxidation reaction can be accelerated. As described above, 1,2,4,5-benzenetetracarboxylic acid and 1,2,3,4-benzenetetracarboxylic acid that are the objective products have a carboxy group that is a hydrophilic group, so that they exist in an aqueous phase after the reaction. Accordingly, by using water as a solvent, when a feedstock derived from petroleum or derived from coal is used, for example, without a step for separation from other hydrophobic hydrocarbons contained in the feedstock, a benzenetetracarboxylic acid that is the objective product can be obtained.

Alternatively, by oxidizing two or more hydrocarbons selected from the group consisting of hydrocarbons having a 1,2,3,4,5,6,7,8-octahydroanthracene skeleton and hydrocarbons having a 1,2,3,4,5,6,7,8-octahydrophenanthrene skeleton by gas phase oxidation while using a solid catalyst such as a divanadium pentaoxide, 1,2,4,5-benzenetetracarboxylic acid and/or 1,2,3,4-benzenetetracarboxylic acid can also be obtained.

When the oxidation reaction step of the present invention is performed by liquid phase oxidation, the reaction temperature is preferably 50 to 150° C. and more preferably 80 to 120° C. When the reaction temperature is higher than 50° C., the oxidation reaction can be satisfactorily progressed. The oxidation reaction is an aqueous phase reaction, so that when the reaction temperature is set at 100° C. or higher, it is necessary to maintain the liquid phase by pressurizing. However, by setting the reaction temperature at lower than 150° C., a pressure necessary for preventing evaporation of water as the solvent can be lowered.

In addition, when the oxidation reaction step is performed by liquid phase oxidation, the reaction pressure is preferably normal pressure to 1 MPa. When the reaction temperature is higher than the boiling point of water as the solvent, pressure of normal pressure or higher is necessary to suppressing loss of water by evaporation, which causes no problem so long as the reaction pressure is a pressure capable of suppressing loss of water.

Accordingly, the method for manufacturing the benzenetetracarboxylic acid of the present invention can exhibit such an effect as capable of obtaining 1,2,4,5-benzenetetracarboxylic acid and/or 1,2,3,4-benzenetetracarboxylic acid with a high yield by a method including: hydrogenating the feedstock, for example, derived from petroleum or derived from coal and containing two or more hydrocarbons selected from the group consisting of tricyclic aromatic hydrocarbons having an anthracene skeleton represented by General Formula (I) and tricyclic aromatic hydrocarbons having a phenanthrene skeleton represented by General Formula (II) using, as a hydrogenation catalyst, a catalyst having two or more active metals selected from the group consisting of nickel, molybdenum, cobalt, and tungsten after the hydrogenation catalyst is subjected to sulfuration treatment (preliminary sulfuration treatment); and oxidizing, with a metal oxide, two or more hydrocarbons selected from the group consisting of hydrocarbons having a 1,2,3,4,5,6,7,8-octahydroanthracene skeleton represented by General Formula (III) and hydrocarbons having a 1,2,3,4,5,6,7,8-octahydrophenanthrene skeleton represented by General Formula (IV) that have been produced by hydrogenation.

Furthermore, when the liquid phase reaction is selected, the liquid phase reaction is generally effected in a two-phase system, so that components of which oxidation is not satisfactorily progressed are separated into an oil phase and the number of components obtained in the same phase (aqueous phase) as the phase in which a benzenetetracarboxylic acid as the objective product exists is considerably limited. Therefore, by using the present invention, from the feedstock derived from petroleum and/or derived from coal containing uncountable components, a benzenetetracarboxylic acid as the objective product can be extremely efficiently obtained.

<Isomerization Reaction Step>

In the method for manufacturing the benzenetetracarboxylic acid of the present invention, after the hydrogenation reaction step and before the oxidation reaction step, there may also be performed an isomerization step for isomerizing the hydrocarbon having a 1,2,3,4,5,6,7,8-octahydrophenanthrene skeleton represented by General Formula (IV) to the hydrocarbon having a 1,2,3,4,5,6,7,8-octahydroanthracene skeleton represented by General Formula (III) using an acid catalyst to increase the ratio of the hydrocarbon having a 1,2,3,4,5,6,7,8-octahydroanthracene skeleton in the feedstock.

1,2,4,5-benzenetetracarboxylic acid is more useful as a feedstock for a polyimide resin and the like than 1,2,3,4-benzenetetracarboxylic acid and it is preferred that the ratio of 1,2,4,5-benzenetetracarboxylic acid in the obtained benzenetetracarboxylic acid becomes higher. Accordingly, by isomerizing the hydrocarbon having a 1,2,3,4,5,6,7,8-octahydrophenanthrene skeleton represented by General Formula (IV) to the hydrocarbon having a 1,2,3,4,5,6,7,8-octahydroanthracene skeleton represented by General Formula (III) using an acid catalyst, the ratio of the hydrocarbon having a 1,2,3,4,5,6,7,8-octahydroanthracene skeleton in the stock oil can be increased and the ratio of the finally obtained 1,2,4,5-benzenetetracarboxylic acid can be enlarged.

As the hydrocarbon having a 1,2,3,4,5,6,7,8-octahydrophenanthrene skeleton to be isomerized, a hydrocarbon having a 1,2,3,4,5,6,7,8-octahydrophenanthrene skeleton prepared by separating a hydrocarbon having a 1,2,3,4,5,6,7,8-octahydrophenanthrene skeleton from a mixture of a hydrocarbon having a 1,2,3,4,5,6,7,8-octahydroanthracene skeleton and a hydrocarbon having a 1,2,3,4,5,6,7,8-octahydrophenanthrene skeleton by various methods may be used.

The isomerization of the hydrocarbon having a 1,2,3,4,5,6,7,8-octahydrophenanthrene skeleton represented by General Formula (IV) to the hydrocarbon having a 1,2,3,4,5,6,7,8-octahydroanthracene skeleton represented by General Formula (III) can be performed by isomerizing to an equilibrium composition between phenanthrene and anthracene.

As the acid catalyst used for the isomerization of the hydrocarbon having a 1,2,3,4,5,6,7,8-octahydrophenanthrene skeleton represented by General Formula (IV) to the hydrocarbon having a 1,2,3,4,5,6,7,8-octahydroanthracene skeleton represented by General Formula (III), besides a silica-alumina-based solid acid catalyst, aluminum chloride and the like can be used.

EXAMPLES

Hereinafter, the present invention is described more in detail referring to Examples that should not be construed as limiting the scope of the present invention.

<Hydrogenation Reaction Step>

Reference Example 1

Into a 300 ml autoclave, 4.0 g of a commercially available cobalt-molybdenum catalyst (catalyst containing 3% by mass of cobalt oxide and 20% by mass of molybdenum oxide, based on the mass of the catalyst and containing alumina as a carrier) and 4.0 g of dimethyl sulfide were charged. Then, into the autoclave, hydrogen was supplied to elevate the pressure in the autoclave to 3.0 MPa. Next, the temperature in the autoclave was elevated to 320° C. and by performing sulfuration treatment for 1 hour, the hydrogenation catalyst was subjected to the sulfuration treatment. Next, into the autoclave containing the catalyst, 12 g of anthracene, 200 ml of n-decane as a solvent, and dibenzothiophene as a sulfur content were charged so that the amount of dibenzothiophene became 0.15% by mass based on the total mass of anthracene and n-decane. Next, into the autoclave, hydrogen was supplied to elevate the pressure in the autoclave to 3 MPa. Then, while stirring the inside of the autoclave, the hydrogenation reaction was effected at a reaction temperature of 320° C. and under a reaction pressure of 5 MPa for 2 hours. After the completion of the reaction, the temperature of the inside of the autoclave was lowered to room temperature and the inside of the autoclave was depressurized. Next, by filtration under reduced pressure, the catalyst was removed from the reaction mixture. Finally, the reaction mixture was analyzed by an FID gas chromatograph (manufactured by Shimadzu Corporation; GC-14B) to measure the yield of 1,2,3,4,5,6,7,8-octahydroanthracene. As the result of the analysis, the conversion of anthracene was 100% and the yield of 1,2,3,4,5,6,7,8-octahydroanthracene as the objective product was 36% by mass.

Reference Example 2

In the same manner as in Reference Example 1, except that the reaction temperature was 300° C., the hydrogenation reaction was effected. The conversion of anthracene was 100% and the yield of 1,2,3,4,5,6,7,8-octahydroanthracene as the objective product was 34% by mass.

Reference Example 3

In the same manner as in Reference Example 1, except that the hydrogenation catalyst was a commercially available nickel-molybdenum catalyst (catalyst containing 3% by mass of nickel oxide and 20% by mass of molybdenum oxide, based on the mass of the catalyst and containing alumina as a carrier), the reaction pressure was 10 MPa, and the reaction time was 1 hour, the hydrogenation reaction was effected. The conversion of anthracene was 100% and the yield of 1,2,3,4,5,6,7,8-octahydroanthracene as the objective product was 45% by mass.

Reference Example 4

In the same manner as in Reference Example 1, except that the hydrogenation catalyst was a commercially available nickel-molybdenum catalyst (catalyst containing 3% by mass of nickel oxide and 20% by mass of molybdenum oxide, based on the mass of the catalyst and containing alumina as a carrier) and the reaction time was 4 hours, the hydrogenation reaction was effected. The conversion of anthracene was 100% and the yield of 1,2,3,4,5,6,7,8-octahydroanthracene as the objective product was 60% by mass.

Reference Example 5

In the same manner as in Reference Example 4, except that the hydrogenation catalyst was a commercially available nickel-tungsten catalyst (catalyst containing 3% by mass of nickel oxide and 20% by mass of tungsten oxide, based on the mass of the catalyst and containing alumina as a carrier), the hydrogenation reaction was effected. The conversion of anthracene was 100% and the yield of 1,2,3,4,5,6,7,8-octahydroanthracene as the objective product was 16% by mass.

Reference Example 6

In the same manner as in Reference Example 4, except that the reaction temperature was 150° C., the hydrogenation reaction was effected. The conversion of anthracene was 2% and the yield of 1,2,3,4,5,6,7,8-octahydroanthracene as the objective product was 1% by mass.

Reference Example 7

Into a 50 ml autoclave, 0.5 g of a commercially available platinum catalyst (catalyst containing 5% by mass of platinum, based on the mass of the catalyst and containing alumina as a carrier), 2 g of anthracene, 15 ml of decalin (mixture of isomers) as a solvent, and dibenzothiophene as a sulfur content were charged so that the amount of dibenzothiophene became 0.15% by mass based on the total mass of anthracene and decalin. Next, into the autoclave, hydrogen was supplied to elevate the pressure in the autoclave to 3 MPa. Next, while stirring the inside of the autoclave, the hydrogenation reaction was effected at a reaction temperature of 150° C. and under a reaction pressure of 7 MPa for 3 hours. After the completion of the reaction, the temperature of the inside of the autoclave was lowered to room temperature and the inside of the autoclave was depressurized. Next, by filtration under reduced pressure, the catalyst was removed from the reaction mixture. Finally, the reaction mixture was analyzed by an FID gas chromatograph (manufactured by Shimadzu Corporation; GC-14B) to measure the yield of 1,2,3,4,5,6,7,8-octahydroanthracene. As the result of the analysis, the conversion of anthracene was 7% and the yield of 1,2,3,4,5,6,7,8-octahydroanthracene as the objective product was 5% by mass.

Reference Example 8

In the same manner as in Reference Example 4, except that the feedstock was 12 g of phenanthrene, the hydrogenation reaction was effected. The conversion of phenanthrene was 95% and the yield of 1,2,3,4,5,6,7,8-octahydrophenanthrene was 49% by mass.

Reference Example 9

In the same manner as in Reference Example 4, except that dibenzothiophene was not added, the hydrogenation reaction was effected. The conversion of anthracene was 100% and the yield of 1,2,3,4,5,6,7,8-octahydroanthracene as the objective product was 60% by mass.

Reference Example 10

In the same manner as in Reference Example 7, except that dibenzothiophene was not added, the hydrogenation reaction was effected. The conversion of anthracene was 99% and the yield of 1,2,3,4,5,6,7,8-octahydroanthracene as the objective product was 77% by mass.

In Table 2, the following results are listed.

"Feedstock": name of the feedstock

"Content of tricyclic aromatic skeleton": content of anthracene or phenanthrene contained in the feedstock (% by mass)

"Active metal of catalyst": type of the active metal contained in the hydrogenation catalyst "Catalyst carrier": type of the carrier of the hydrogenation catalyst "Addition of sulfur content": whether dibenzothiophene was added to the feedstock or not (when dibenzothiophene was added, dibenzothiophene was added so that the amount of dibenzothiophene became 0.15% by mass based on the total mass of the feedstock and the solvent).

"Reaction temperature": reaction temperature for hydrogenation reaction (° C.)

"Reaction pressure": reaction pressure for hydrogenation reaction (MPa)

"Reaction time": reaction time for hydrogenation reaction (h)

"Conversion": hydrogenation conversion of the tricyclic aromatic hydrocarbons having an anthracene skeleton and/or a phenanthrene skeleton that can be used in the present invention (%)

"Yield of 8H body": ratio of obtained 1,2,3,4,5,6,7,8-octahydroanthracene skeleton or obtained 1,2,3,4,5,6,7,8-octahydrophenanthrene skeleton (% by mass)

In the case of Reference Examples 9 to 10 in which the feedstock contained no sulfur content, it was confirmed that both when the catalyst was a noble metal catalyst and when the catalyst was a catalyst containing, as an active metal, two or more types selected from nickel, cobalt, molybdenum, and tungsten, an 8H body could be obtained with advantageous selectivity. On the other hand, with respect to Reference Examples 1 to 8 in which the feedstock contained sulfur content, it became apparent that in comparison with that the conversion of the tricyclic aromatic hydrocarbon and the yield of an 8H body were extremely low in Reference Example 7 using a noble metal catalyst, in Reference Examples 1 to 5 and Reference Example 8 using a catalyst containing, as an active metal, two or more types selected from nickel, cobalt, molybdenum, and tungsten, the yield of an 8H body was high and a large amount of an 8H body could be obtained. In addition, even when a nickel-molybdenum catalyst was used, it was confirmed that in Reference Example 6 in which the reaction temperature was low, the yield of an 8H body was low, so that a higher reaction temperature was necessary.

Example 1

Into a 300 ml autoclave, 4.0 g of a commercially available nickel-molybdenum catalyst (catalyst containing 3% by mass of nickel oxide and 20% by mass of molybdenum oxide, based on the mass of the catalyst and containing alumina as a carrier) and 4.0 g of dimethyl sulfide were charged. Then, into the autoclave, hydrogen was supplied to elevate the pressure in the autoclave to 3.0 MPa. Next, the temperature in the autoclave was elevated to 320° C. and by performing sulfuration treatment for 1 hour, the hydrogenation catalyst was subjected to the sulfuration treatment. Next, into the autoclave containing the catalyst, 6 g of anthracene, 6 g of phenanthrene, 200 ml of n-decane as a solvent, and dibenzothiophene as a sulfur content were charged so that the amount of dibenzothiophene became 0.15% by mass based

TABLE 2

| | Ref. Ex. 1 | Ref. Ex. 2 | Ref. Ex. 3 | Ref. Ex. 4 | Ref. Ex. 5 | Ref. Ex. 6 | Ref. Ex. 7 | Ref. Ex. 8 | Ref. Ex. 9 | Ref. Ex. 10 |
|---|---|---|---|---|---|---|---|---|---|---|
| Feedstock | Anthracene | | | | | | | Phenanthrene | Anthracene | |
| Content of tricyclic aromatic skeleton (% by mass) | | | | | | 100 | | | | |
| Active metal of catalyst | Co, Mo | Co, Mo | Ni, Mo | Ni, Mo | Ni, W | Ni, Mo | Pt | Ni, Mo | Ni, Mo | Pt |
| Catalyst carrier | | | | | | $Al_2O_3$ | | | | |
| Addition of sulfur content | Yes | Yes | Yes | Yes | Yes | Yes | Yes | Yes | No | No |
| Reaction temperature (° C.) | 320 | 300 | 320 | 320 | 320 | 150 | 150 | 320 | 320 | 150 |
| Reaction pressure (MPa) | 5 | 5 | 10 | 5 | 5 | 5 | 7 | 5 | 5 | 7 |
| Reaction time (h) | 2 | 2 | 1 | 4 | 4 | 4 | 3 | 4 | 4 | 3 |
| Conversion (%) | 100 | 100 | 100 | 100 | 100 | 2 | 7 | 95 | 100 | 99 |
| Yield of 8H body (% by mass) | 36 | 34 | 45 | 60 | 16 | 1 | 5 | 49 | 60 | 77 | on the total mass of anthracene, phenanthrene and n-decane. Next, into the autoclave, hydrogen was supplied to elevate the pressure in the autoclave to 3 MPa. Then, while stirring the inside of the autoclave, the hydrogenation reaction was effected at a reaction temperature of 320° C. and under a reaction pressure of 5 MPa for 4 hours. After the completion of the reaction, the temperature in the autoclave was lowered to room temperature and the inside of the autoclave was depressurized. Next, by filtration under reduced pressure, the catalyst was removed from the reaction mixture. Finally, the reaction mixture was analyzed by an FID gas chromatograph (manufactured by Shimadzu Corporation; GC-14B) to measure the conversion of the tricyclic aromatic hydrocarbon and the yield of the objective reaction products (8H body: 1,2,3,4,5,6,7,8-octahydroanthracene and 1,2,3,4,5,6,7,8-octahydrophenanthrene). As the result of the analysis, 97% of the mixture of anthracene and phenanthrene was hydrogenated and the yield of 1,2,3,4,5,6,7,8-octahydroanthracene and 1,2,3,4,5,6,7,8-octahydrophenanthrene as the objective products was 52% by mass. Here, the yield of 1,2,3,4,5,6,7,8-octahydroanthracene from anthracene was 54% by mass and the yield of 1,2,3,4,5,6,7,8-octahydrophenanthrene from phenanthrene was 50% by mass.

Example 2

A heavy oil (cracking product obtained from an FCC units) having general properties listed in Table 3 was analyzed using a two-dimensional gas chromatograph system (manufactured by ZOEX CORPORATION; KT2006 GC×GC System) and the content of tricyclic aromatic hydrocarbons having an anthracene skeleton and a phenanthrene skeleton that can be used in the present invention in the heavy oil was 21% by mass. In the same manner as in Example 1, except that as the feedstock, 200 ml of the heavy oil (having a sulfur content of 0.17% by mass) was used and n-decane and dibenzothiophene were not added, the hydrogenation reaction was effected. After the completion of the reaction, using the two-dimensional gas chromatograph system (manufactured by ZOEX CORPORATION; KT2006 GC×GC System), the reaction mixture was analyzed and as the result thereof, the conversion of the tricyclic aromatic hydrocarbon contained in the heavy oil was 100% and the yield of hydrocarbons having a 1,2,3,4,5,6,7,8-octahydro anthracene skeleton and a 1,2,3,4,5,6,7,8-octahydrophenanthrene skeleton was 54% by mass.

Comparative Example 1

Into a 50 ml autoclave, 0.5 g of a commercially available platinum catalyst (catalyst containing 5% by mass of platinum based on the mass of the catalyst and containing alumina as a carrier) and 17 ml of the heavy oil having general properties listed in Table 3 were charged. Next, into the autoclave, hydrogen was supplied to elevate the pressure in the autoclave to 3 MPa. Next, while stirring the inside of the autoclave, the hydrogenation reaction was effected at a reaction temperature of 150° C. and under a reaction pressure of 7 MPa for 3 hours. After the completion of the reaction, the temperature in the autoclave was lowered to room temperature and the inside of the autoclave was depressurized. Next, by filtration under reduced pressure, the catalyst was removed from the reaction mixture. Finally, the reaction mixture was analyzed using a two-dimensional gas chromatograph system (manufactured by ZOEX CORPORATION; KT2006 GC×GC System) and as the result of the analysis, the conversion of the tricyclic aromatic hydrocarbon contained in the heavy oil was 8% and the yield of hydrocarbons having a 1,2,3,4,5,6,7,8-octahydro anthracene skeleton and a 1,2,3,4,5,6,7,8-octahydrophenanthrene skeleton was 6% by mass.

TABLE 3

| Feedstock properties | | | | Analysis method |
|---|---|---|---|---|
| Density (15° C.) | | g/cm$^3$ | 0.9481 | JIS K 2249 |
| Kinematic viscosity (30° C.) | | mm$^2$/s | 11.67 | JIS K 2283 |
| Sulfur content | | % by mass | 0.17 | JIS K 2541 |
| Distillation properties | 10% by volume distillation temperature | ° C. | 275.4 | JIS K 2254 |
| | 50% by volume distillation temperature | ° C. | 347.7 | |
| | 90% by volume distillation temperature | ° C. | 392.1 | |
| | End point | ° C. | 439.5 | |
| Composition analysis | Saturated hydrocarbons content | % by volume | 30.3 | JPI-5S-49 |
| | Olefins content | % by volume | 1.1 | |
| | All aromatic hydrocarbons content | % by volume | 68.6 | |
| | Monocyclic aromatic hydrocarbons content | % by volume | 5.6 | |
| | Bicyclic aromatic hydrocarbons content | % by volume | 19.2 | |
| | Tri- or more cyclic aromatic hydrocarbons content | % by volume | 43.8 | |

In Table 4, the following results are listed.

"Feedstock": name of the feedstock

"Content of tricyclic aromatic skeleton": content of tricyclic aromatic hydrocarbons having anthracene skeleton and/or phenanthrene skeleton that can be used in the present invention and that were contained in the feedstock (% by mass)

"Active metal of catalyst": type of the active metal contained in the hydrogenation catalyst "Catalyst carrier": type of the carrier of the hydrogenation catalyst "Reaction temperature": reaction temperature for hydrogenation reaction (° C.)

"Reaction pressure": reaction pressure for hydrogenation reaction (MPa)

"Reaction time": reaction time for hydrogenation reaction (h)

"Conversion": hydrogenation conversion ratio of tricyclic aromatic hydrocarbons having an anthracene skeleton and/or a phenanthrene skeleton that can be used in the present invention (%)

"Yield of 8H body": ratio of obtained hydrocarbons having 1,2,3,4,5,6,7,8-octahydroanthracene skeleton and/or 1,2,3,4,5,6,7,8-octahydrophenanthrene skeleton that can be used in the present invention (% by mass)

TABLE 4

|  | Example 1 | Example 2 | Comparative Example 1 |
|---|---|---|---|
| Feedstock | Anthracene + phenanthrene | Heavy oil | |
| Content of tricyclic aromatic skeleton (% by mass) | 100 (50/50) | 21 | |
| Active metal of catalyst | Ni, Mo | Ni, Mo | Pt |
| Catalyst carrier |  | $Al_2O_3$ |  |
| Addition of sulfur content | Yes | — | — |
| Reaction temperature (° C.) | 320 | 320 | 150 |
| Reaction pressure (MPa) | 5 | 5 | 7 |
| Reaction time (h) | 4 | 4 | 3 |
| Conversion (%) | 97 | 100 | 8 |
| Yield of 8H body (% by mass) | 52 | 54 | 6 |

It became apparent that although in Comparative Example 1 using a noble metal catalyst, the catalyst was affected by a sulfur content contained in the heavy oil, so that the conversion of the tricyclic aromatic hydrocarbon and the yield of the 8H body were extremely low, on the contrary, in Examples 1 to 2 using a catalyst having nickel and molybdenum as active metals, the catalyst was not affected by the sulfur content and the conversion of the tricyclic aromatic hydrocarbon and the yield of the 8H body were high, so that a large amount of the 8H body that can be used in the present invention could be obtained.

<Oxidation Reaction Step>

Reference Example 11

Into a 300 ml separable flask, 240 ml of water and 26.8 g of potassium permanganate were charged. Next, the resultant mixture was heated to 70° C. and was stirred until potassium permanganate was dissolved. Then, to the resultant solution, sodium dodecylbenzenesulfonate ((DBS)-Na) in an amount of 1.0% by mole relative to potassium permanganate and 1.87 g of 1,2,3,4,5,6,7,8-octahydrophenanthrene were added and while stirring the resultant reaction mixture at 95° C. for 50 hours, the oxidation reaction was effected. After the completion of the reaction, the reaction mixture was analyzed using a liquid chromatograph (manufactured by Shimadzu Corporation; SPD-10A, LC-10AD) to measure the yield of 1,2,3,4-benzenetetracarboxylic acid. As the result of the analysis, 1,2,3,4-benzenetetracarboxylic acid was obtained in a yield of 82% by mass.

Reference Example 12

Into a 200 ml beaker, 1.7 g of manganese (II) sulfate tetrahydrate and 30 ml of water were charged and the resultant mixture was heated to 85° C. and stirred until manganese (II) sulfate tetrahydrate was dissolved. Then, to the resultant solution, 7.0 g of sodium dodecylbenzenesulfonate and 100 ml of water were added and the resultant mixture was heated at 85° C. for 10 minutes to dissolve sodium dodecylbenzenesulfonate. The sample in the 200 ml beaker was transferred into a 300 ml beaker and into the 300 ml beaker, furthermore, 70 ml of water was charged to precipitate a light pink color crystal. By filtration, the crystal was separated to obtain manganese (II) dodecylbenzenesulfonate ($(DES)_2Mn$).

Next, into a 300 ml separable flask, 240 ml of water and 26.8 g of potassium permanganate were charged. Next, the resultant mixture was heated to 70° C. and was stirred until potassium permanganate was dissolved. Then, to the resultant solution, manganese (II) dodecylbenzenesulfonate prepared as described above in an amount of 0.5% by mole relative to potassium permanganate was added. Further to the resultant mixture, 1.87 g of 1,2,3,4,5,6,7,8-octahydrophenanthrene was added and while stirring the resultant reaction mixture at 95° C. for 50 hours, the oxidation reaction was effected. After the completion of the reaction, the reaction mixture was analyzed using a liquid chromatograph (manufactured by Shimadzu Corporation; SPD-10A, LC-10AD) to measure the yield of 1,2,3,4-benzenetetracarboxylic acid. As the result of the analysis, 1,2,3,4-benzenetetracarboxylic acid was obtained in a yield of 85% by mass.

Reference Example 13

In the same manner as in Reference Example 12, except that the addition amount of manganese (II) dodecylbenzenesulfonate was changed to 1.0% by mole relative to potassium permanganate and the reaction temperature was changed to 80° C., the oxidation reaction was effected. As the result of the analysis, 1,2,3,4-benzenetetracarboxylic acid was obtained in a yield of 75% by mass.

Reference Example 14

In the same manner as in Reference Example 12, except that the feedstock was changed to 1.87 g of the anthracene hydrogenated product (with the proviso that it was prepared by removing n-decane by distillation beforehand and it contained 60% of 1,2,3,4,5,6,7,8-octahydroanthracene) obtained in Reference Example 4, the oxidation reaction was effected. As the result of the analysis, 1,2,4,5-benzenetetracarboxylic acid was obtained in a yield of 59% by mass.

Reference Example 15

Into a 50 ml autoclave, 1.0 g of 1,2,3,4,5,6,7,8-octahydrophenanthrene, 2.18 mg of cobalt acetate ($Co(OAc)_2$), 16.4 mg of manganese acetate tetrahydrate ($Mn(OAc)_2 \cdot 4H_2O$), and 12.0 ml of acetic acid were charged and the inside of the reaction system was purged with air. Then, the temperature in the reaction system was elevated to 150° C. and the pressure in the reaction system was adjusted to 2.0 MPa. In this state, using oxygen in the air as an oxidant, the oxidation reaction was effected for 6 hours. After the completion of the reaction, the temperature in the reaction system was lowered to room temperature and the reaction mixture was analyzed using a liquid chromatograph (manufactured by Shimadzu Corporation; SPD-10A, LC-10AD) to measure the yield of 1,2,3,4-benzenetetracarboxylic acid. As the result of the analysis, 1,2,3,4-benzenetetracarboxylic acid was obtained in a yield of 1% by mass.

In Table 5, the following results are listed.

"Feedstock": name of the feedstock

"Content of 8H body": content of having 1,2,3,4,5,6,7,8-octahydroanthracene or 1,2,3,4,5,6,7,8-octahydrophenanthrene (% by mass)

"Oxidant": type of oxidant

"Solvent": solvent for oxidation reaction

"Reaction temperature": reaction temperature for oxidation reaction (° C.)

"Reaction pressure": reaction pressure for oxidation reaction (MPa)

"Oxidation catalyst or additive": additive or catalyst added to reaction mixture during oxidation reaction; in case of additive, ratio of additive relative to oxidant and in case of catalyst, ratio of catalyst relative to feedstock (% by mole)

"Reaction time": reaction time for which oxidation reaction was effected (h)

"Yield of BTC": yield of obtained 1,2,3,4-benzenetetracarboxylic acid or obtained 1,2,4,5-benzenetetracarboxylic acid (% by mass)

TABLE 5

|  | Ref. Ex. 11 | Ref. Ex. 12 | Ref. Ex. 13 | Ref. Ex. 14 | Ref. Ex. 15 |
|---|---|---|---|---|---|
| Feedstock | 1,2,3,4,5,6,7,8-octahydrophenanthrene | | | Anthracene hydrogenated product | 1,2,3,4,5,6,7,8-octahydrophenanthrene |
| Content of 8H body (% by mass) | 100 | | | 60 | 100 |
| Oxidant | $KMnO_4$ | $KMnO_4$ | $KMnO_4$ | $KMnO_4$ | Oxygen |
| Solvent | Water | Water | Water | Water | Acetic acid |
| Reaction temperature (° C.) | 95 | 95 | 80 | 95 | 150 |
| Reaction pressure (MPa) | 0 | 0 | 0 | 0 | 2.0 |
| Oxidation catalyst or additive (% by mole) (in case of additive, relative to oxidant) | (DBS)-Na 1.0 | $(DBS)_2Mn$ 0.5 | $(DBS)_2Mn$ 1.0 | $(DBS)_2Mn$ 0.5 | $Co(OAc)_2$ 0.28 $Mn(OAc)_2 \cdot 4H_2O$ 1.4 |
| Reaction time (h) | 50 | 50 | 50 | 50 | 6 |
| Yield of BTC (% by mass) | 82 | 85 | 75 | 59 | 1 |

It became apparent that although in Reference Example 15 not using a strong oxidant, the yield of BTC was extremely low, on the contrary, in Reference Examples 11 to 14 using as an oxidant, potassium permanganate that is a metal oxide having a strong oxidizability, the yield of BTC was extremely high and BTC could be efficiently generated.

Example 3

Into a 200 ml beaker, 1.7 g of manganese (II) sulfate tetrahydrate and 30 ml of water were charged and the resultant mixture was heated to 85° C. and stirred until manganese (II) sulfate tetrahydrate was dissolved. Then, to the resultant solution, 7.0 g of sodium dodecylbenzenesulfonate and 100 ml of water were added and the resultant mixture was heated at 85° C. for 10 minutes to dissolve sodium dodecylbenzenesulfonate. The sample in the 200 ml beaker was transferred into a 300 ml beaker and into the 300 ml beaker, furthermore, 70 ml of water was charged to precipitate a light pink color crystal. By filtration, the crystal was separated to obtain manganese (II) dodecylbenzenesulfonate (($DBS)_2Mn$).

Next, into a 300 ml separable flask, 240 ml of water and 26.8 g of potassium permanganate were charged. Next, the resultant mixture was heated to 70° C. and the mixture was stirred until potassium permanganate was dissolved. Then, to the resultant solution, manganese (II) dodecylbenzenesulfonate prepared as described above in an amount of 1.0% by mole relative to potassium permanganate was added. Furthermore, to the resultant mixture, 1.87 g of the hydrogenated product (with the proviso that it was prepared by removing n-decane by distillation beforehand and it contained 52% by mass of 1,2,3,4,5,6,7,8-octahydroanthracene and 1,2,3,4,5,6,7,8-octahydrophenanthrene) of the mixture (mass ratio: 1:1) of anthracene and phenanthrene that was obtained in Example 1 was added and while stirring the resultant reaction mixture at 95° C. for 50 hours, the oxidation reaction was effected. After the completion of the reaction, the reaction mixture was analyzed using a liquid chromatograph (manufactured by Shimadzu Corporation; SPD-10A, LC-10AD) to measure the yield of 1,2,3,4-benzenetetracarboxylic acid and 1,2,4,5-benzenetetracarboxylic acid. As the result of the analysis, 1,2,3,4-benzenetetracarboxylic acid and 1,2,4,5-benzenetetracarboxylic acid were obtained in a yield of total 53% by mass.

Example 4

In the same manner as in Example 3, except that the feedstock was changed to 8.3 ml of the hydrogenated product of the heavy oil that was obtained in Example 2, the oxidation reaction was effected. As the result of the analysis, 1,2,3,4-benzenetetracarboxylic acid and 1,2,4,5-benzenetetracarboxylic acid were obtained in a yield of total 50% by mass.

In Table 6, the following results are listed.

"Feedstock": name of the feedstock "Content of 8H body": content of hydrocarbons having 1,2,3,4,5,6,7,8-octahydroanthracene skeleton and/or 1,2,3,4,5,6,7,8-octahydrophenanthrene skeleton that can be used in the present invention in feedstock (% by mass)

"Oxidant": type of oxidant

"Solvent": solvent for oxidation reaction "Reaction temperature": reaction temperature for oxidation reaction (° C.) "Reaction pressure": reaction pressure for oxidation reaction (MPa) "Additive": name of additive added during oxidation reaction and addition amount thereof relative to oxidant (% by mole)

"Reaction time": reaction time for which oxidation reaction was effected (h) "Yield of BTC": ratio of obtained 1,2,3,4-benzenetetracarboxylic acid and/or obtained 1,2,4,5-benzenetetracarboxylic acid (% by mass)

TABLE 6

|  | Example 3 | Example 4 |
|---|---|---|
| Feedstock | Anthracene hydrogenated product + phenanthrene hydrogenated product | Heavy oil hydrogenated product |
| Content of 8H body (% by mass) | 52 | 11 |
| Oxidant | $KMnO_4$ | $KMnO_4$ |
| Solvent | Water | Water |

TABLE 6-continued

|  | Example 3 | Example 4 |
|---|---|---|
| Reaction temperature (° C.) | 95 | 95 |
| Reaction pressure (MPa) | 0 | 0 |
| Additive (% by mole) | (DBS)$_2$Mn 1.0 | (DBS)$_2$Mn 1.0 |
| Reaction time (h) | 50 | 50 |
| Yield of BTC (% by mass) | 53 | 50 |

It became apparent that in Examples 3 and 4 using, as an oxidant, potassium permanganate that is a metal oxide having a strong oxidizability, the yield of BTC was high and BTC could be efficiently generated.

<Isomerization Reaction Step>

A reaction tube was filled with 2.0 ml of a commercially available granular silica-alumina catalyst (silica/alumina ratio: 6.5) and the temperature in the reaction tube was elevated to 250° C. Next, into the reaction tube, 1,2,3,4,5,6,7,8-octahydrophenanthrene was supplied at 6.0 ml/h. At this time, the liquid hourly space velocity was 3 h$^{-1}$. Then, after 10 minutes from the reaction initiation, the reaction product discharged through an outlet of the reaction tube was recovered and was analyzed by an FID gas chromatograph (manufactured by Shimadzu Corporation; GC-14B).

As the result of the above isomerization reaction, 1,2,3,4,5,6,7,8-octahydroanthracene was obtained in a yield of 19% by mass. From this result, it became apparent that by the isomerization step, it was possible to convert a hydrocarbon having a 1,2,3,4,5,6,7,8-octahydrophenanthrene skeleton represented by General Formula (IV) into a hydrocarbon having a 1,2,3,4,5,6,7,8-octahydroanthracene skeleton represented by General Formula (III) and it was also possible to increase the ratio of 1,2,4,5-benzenetetracarboxylic acid in the benzenetetracarboxylic acid as the objective product.

INDUSTRIAL APPLICABILITY

As described above, the method for manufacturing a benzenetetracarboxylic acid according to the present invention has an industrially practicable form and is useful for effective utilization of a heavy fraction containing a tricyclic aromatic hydrocarbon.

The invention claimed is:

1. A method for manufacturing a benzenetetracarboxylic acid, comprising:
   (1) a hydrogenation reaction step to generate, by hydrogenating a feedstock comprising at least two hydrocarbons selected from the group consisting of:
      (a) tricyclic aromatic hydrocarbons having an anthracene skeleton represented by Formula (I):

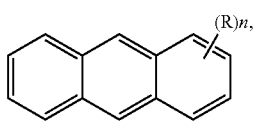

(I)

wherein R is a linear or branched alkyl group and n represents the number of substituents on the anthracene skeleton and is an integer of 2 to 8, with the proviso that R is located at the 1-position to the 8-position and Rs are optionally alkyl groups having the same number of or different numbers of carbon atoms, and (b) tricyclic aromatic hydrocarbons having a phenanthrene skeleton represented by Formula (II):

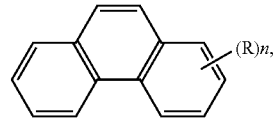

(II)

wherein R is a linear or branched alkyl group and n represents the number of substituents on the phenanthrene skeleton and is an integer of 2 to 8, with the proviso that R is located at the 1-position to the 8-position and Rs are optionally alkyl groups having the same number of or different numbers of carbon atoms, at least two hydrocarbons selected from the group consisting of:
   (a) hydrocarbons having a 1,2,3,4,5,6,7,8-octahydroanthracene skeleton represented by Formula (III):

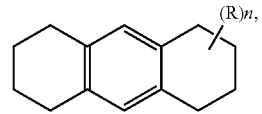

(III)

wherein R is a linear or branched alkyl group and n represents the number of substituents on the 1,2,3,4,5,6,7,8-octahydroanthracene skeleton and is an integer of 2 to 8, with the proviso that R is located at the 1-position to the 8-position and Rs are optionally alkyl groups having the same number of or different numbers of carbon atoms, and (b) hydrocarbons having a 1,2,3,4,5,6,7,8-octahydrophenanthrene skeleton represented by Formula (IV):

(IV)

wherein R is a linear or branched alkyl group and n represents the number of substituents on the 1,2,3,4,5,6,7,8-octahydrophenanthrene skeleton and is an integer of 2 to 8, with the proviso that R is located at the 1-position to the 8-position and when n is 2 to 8, Rs are optionally alkyl groups having the same number of or different numbers of carbon atoms, using, as a hydrogenation catalyst, a catalyst containing at least two active metals selected from the group consisting of nickel, molybdenum, cobalt, and tungsten; and (2) an oxidation reaction step to oxidize, with a metal oxide, the at least two hydrocarbons selected from the group consisting of (a) hydrocarbons having the 1,2,3,4,5,6,7,8-octahydroanthracene skeleton represented by the Formula (III) and (b) hydrocarbons having the 1,2,3,4,5,6,7,8-octahydrophenanthrene skeleton represented by the Formula (IV) that are generated in (1) the hydrogenation reaction step.

2. The method for manufacturing the benzenetetracarboxylic acid according to claim 1, wherein in Formulae (I), (II), (III), and (IV), R is a C$_{1-4}$ linear or branched alkyl group.

3. The method for manufacturing the benzenetetracarboxylic acid according to claim 1, wherein in Formulae (I), (II), (III), and (IV), R is a $C_{1-4}$ linear or branched alkyl group and n is an integer of 2 to 4.

4. The method for manufacturing the benzenetetracarboxylic acid according to claim 1, wherein the feedstock contains a fraction at 340 to 420° C.

5. The method for manufacturing the benzenetetracarboxylic acid according to claim 1, wherein the feedstock is derived from petroleum or coal.

6. The method for manufacturing the benzenetetracarboxylic acid according to claim 1, wherein the metal oxide is potassium permanganate or potassium dichromate.

7. The method for manufacturing the benzenetetracarboxylic acid according to claim 1, wherein (1) the hydrogenation reaction step further comprises selectively hydrogenating the feedstock with the hydrogenation catalyst in the presence of hydrogen at a reaction temperature of 200 to 400° C. and under a reaction pressure of 2 to 15 MPa.

8. The method for manufacturing the benzenetetracarboxylic acid according to claim 1, wherein (2) the oxidation reaction step comprises oxidizing the at least two hydrocarbons of formulae (III) and (IV) generated in the (1) hydrogenation reaction step with the metal oxide in the presence of an additive at a reaction temperature of 50 to 150° C. and under a reaction pressure of normal pressure to 1 MPa.

9. The method for manufacturing the benzenetetracarboxylic acid according to claim 1, further comprising, before (2) the oxidation reaction step:
an isomerization reaction step to isomerize a hydrocarbon having the 1,2,3,4,5,6,7,8-octahydrophenanthrene skeleton represented by the Formula (IV) to a hydrocarbon having a 1,2,3,4,5,6,7,8-octahydroanthracene skeleton represented by the Formula (III), with an acid catalyst.

10. The method for manufacturing the benzenetetracarboxylic acid according to claim 9, wherein in the Formulae (IV) and (III), R is a $C_{1-4}$ linear or branched alkyl group.

11. The method for manufacturing the benzenetetracarboxylic acid according to claim 9, wherein in the Formulae (IV) and (III), R is a $C_{1-4}$ linear or branched alkyl group and n is an integer of 2 to 4.

* * * * *